United States Patent
Liu et al.

(10) Patent No.: US 10,524,818 B2
(45) Date of Patent: Jan. 7, 2020

(54) DOUBLE-JOINT SICKLE KNIFE FOR ENDOSCOPY THERAPY

(71) Applicant: HARBIN MEDICAL UNIVERSITY, Harbin (CN)

(72) Inventors: Bingrong Liu, Harbin (CN); Lixia Zhao, Harbin (CN); Bing Du, Harbin (CN); Yaju Du, Harbin (CN); Lingjian Kong, Harbin (CN); Shui Liu, Harbin (CN)

(73) Assignee: HARBIN MEDICAL UNIVERSITY, Harbin (CN)

( * ) Notice: Subject to any disclaimer, the term of this patent is extended or adjusted under 35 U.S.C. 154(b) by 385 days.

(21) Appl. No.: 15/072,471

(22) Filed: Mar. 17, 2016

(65) Prior Publication Data

US 2016/0270812 A1 Sep. 22, 2016

(30) Foreign Application Priority Data

Mar. 19, 2015 (CN) .......................... 2015 1 0121464

(51) Int. Cl.
*A61B 17/32* (2006.01)
*A61B 17/3211* (2006.01)
*A61B 17/00* (2006.01)

(52) U.S. Cl.
CPC .. *A61B 17/320016* (2013.01); *A61B 17/3211* (2013.01); *A61B 2017/00269* (2013.01); *A61B 2017/32004* (2013.01); *A61B 2017/320052* (2013.01)

(58) Field of Classification Search
CPC ........ A61B 17/320016; A61B 17/3211; A61B 2017/00269; A61B 2017/32004; A61B 2017/320052; B26B 1/00; B26B 1/02; B26B 1/044; B26B 1/06
See application file for complete search history.

(56) References Cited

U.S. PATENT DOCUMENTS

| | | | | |
|---|---|---|---|---|
| 2006/0174898 A1* | 8/2006 | Brown | ............. | A61B 17/32001 128/899 |
| 2008/0029574 A1* | 2/2008 | Shelton | ............ | A61B 17/07207 227/175.2 |
| 2008/0262492 A1* | 10/2008 | Lee | .................. | A61B 17/00234 606/41 |
| 2010/0286686 A1* | 11/2010 | Hancock | ................ | A61B 18/18 606/33 |

(Continued)

*Primary Examiner* — Kathleen S Holwerda
*Assistant Examiner* — Brooke Labranche
(74) *Attorney, Agent, or Firm* — Rankin, Hill & Clark LLP

(57) ABSTRACT

A double-joint sickle knife for an endoscopy therapy includes a knife head, a knife base, a knife body, an outer sheath, a guide wire, a handle and a sliding rod. The knife head is connected with one end of the knife base by a transverse joint, and the other end of the knife base is connected with a head end of the knife body by a longitudinal joint. The outer sheath is sleeved on the outside of the knife body and capable of sliding along the knife body. The tail end of the knife body is connected with one end of the handle, and a sliding rod for adjusting the transverse joint is arranged on the handle. The guide wire is electric conductive. One end of the guide wire is connected with the knife head, and passes through the knife base, the knife body, the handle and the sliding rod successively. The other end of the guide wire is connected with the power port.

8 Claims, 3 Drawing Sheets

(56) References Cited

U.S. PATENT DOCUMENTS

2012/0197253 A1* 8/2012 Nishimura ............ A61B 17/29
   606/46
2012/0215243 A1* 8/2012 Fujii .................. A61B 17/2202
   606/169

* cited by examiner

DOUBLE-JOINT SICKLE KNIFE FOR ENDOSCOPY THERAPY

TECHNICAL FIELD

The present invention relates to a double-joint sickle knife for an endoscopy therapy.

BACKGROUND

With the development of the techniques of digestion endoscope, adaptable indications for endoscopic microsurgeries extends continuously, and relevant minimally invasive techniques such as EMR, ESD, POEM and so on are emerging and developing continuously. The endoscopic submucosal dissection (ESD) therapy is currently an important means of surgical treatment of early gastrointestinal cancers and precancerous lesions. ESD has shown great advantages such as a tiny trauma, a maintenance of organ functions, a quick recovery after the surgery. However, ESD has a high demand in technology, and is prone to come out with complications such as perforation, so that ESD is greatly limited and has not been widely applied. Existing HOOK knifes and IT knifes are an important tool to promote technological development. However, in practice, shortcomings still exist, for example: the angle between knife body and the plane of the therapy view field is a larger angle (approximately vertical), and electrosurgical excision operation easily causes to cut too deeply or even causes perforation, so that the surgical operation is very difficult, and has a higher risk. In addition, the knife body is rod-shaped, so that passive cutting and movement of the knife head is achieved by necessarily moving the endoscope controlled by a surgeon. The above mentioned difficulties highly require a high skill and proficiency for the surgeon.

SUMMARY OF THE INVENTION

In order to solve the above problems in the prior art, the present invention provides a double-joint sickle knife for an endoscopy therapy, which will be achieved by the following technical solutions:

A double-joint sickle knife for an endoscopy therapy, wherein, the knife comprises a knife head, a knife base, a knife body, a guide wire, a handle and a sliding rod; wherein the knife head is connected with one end of the knife base by a transverse joint, and the other end of the knife base is connected with a head end of the knife body by a longitudinal joint; the tail end of the knife body is connected with one end of the handle, and the sliding rod is arranged on the handle; one end of the guide wire is connected with the knife head, and the guide wire passes through the knife base, the knife body, the handle and the sliding rod successively; and the other end of the guide wire is connected with a power port.

The double-joint sickle knife for an endoscopy therapy, wherein, the knife head comprises a knife edge, a knife back and a knife head root.

The double-joint sickle knife for an endoscopy therapy, wherein, the knife back is made of an insulating ceramic material; and the knife edge is made from a metallic material.

The double-joint sickle knife for an endoscopy therapy, wherein: the head end of the guide wire forms the knife edge; one end of the knife base connected with the knife head is divided into two up and down clamping pieces which are parallel to each other; and the space between the two clamping pieces forms a knife groove; one end of the knife head connected with the knife base is a knife head root; and the knife head root is putted into the knife groove; and the knife head root is equipped with a knife head shaft; and the knife head shaft is embedded with the two clamping pieces; a side of the knife head root near the knife back is connected with the knife base by the compression spring; and all the above-mentioned structures form the transverse joint.

The double-joint sickle knife for an endoscopy therapy, wherein: one end of the knife body connected with the knife base is equipped with two shaft bases; a concave base shaft groove is arranged in the middle of the tail end of the knife base; the knife base shaft crosses the one end of the knife body connected with the knife base and protrudes outwardly; and both ends of the knife base shaft are inserted into the two shaft bases respectively; a torsion spring wraps around the knife base shaft and is put into the base shaft groove; two forwardly and backwardly protruding branches of the torsion spring are inserted into the knife base and the knife body respectively; all the above mentioned structures form the longitudinal joint.

The double-joint sickle knife for an endoscopy therapy, wherein: a guide-wire cavity is arranged in the knife body, and the guide wire is arranged in the guide-wire cavity.

The double-joint sickle knife for an endoscopy therapy, wherein, a guide-wire channel is arranged on the knife base and the knife body, and the guide-wire channel is connected with the guide-wire cavity.

The double-joint sickle knife for an endoscopy therapy, wherein, an outer sheath is sleeved on the outside of the knife body, and the outer sheath can move on the knife body and wrap the knife head.

The double-joint sickle knife for an endoscopy therapy, wherein, the sliding rod is H-shaped; and the middle part of the sliding rod is annular and cylindrical, and covers around the outside of the handle; a hollow sliding groove is arranged in the handle; and a rectangular column sliding rod core is arranged in the middle of the sliding rod; and the sliding rod core crosses into the sliding groove; and a guide-wire outlet is arranged at the top of the sliding rod core; and the guide wire passes through the upper end of the sliding rod by the guide-wire outlet and is connected with the power port.

The double-joint sickle knife for an endoscopy therapy, wherein, and the other end of the handle is connected with a round pull ring.

Compared with the prior art, the advantages of the present invention using the above-mentioned technical solutions is that:

1. The sickle knife has two rotary joints. The longitudinal joint can cut tissues by the knife head in parallel with the therapy view field. Therefore, it is highly safe, and can reduce the probability of perforation. The transverse joint facilitates the knife head to actively cut and move in control of the handle and the sliding rod, so that the surgeon finishes cutting tissues without controlling the movement of the lens end of the endoscope in a large range, and thus the difficulty of the therapy is decreased significantly, the efficiency of the therapy is enhanced, and the surgery becomes more easier;

2. The knife head is shaped like a sickle, and just one side of the knife head has a cutting function, and any other side is wrapped around by a ceramic material, so that the knife head can cut mucosal tissues quickly and safely. And thus, subsidiary injuries potentially occurring to peripheral tissues are minimized to the furthest;

3. Subsidiary injuries in endoscopy microsurgeries such as endoscopic submucosal dissection (ESD) can be greatly reduced. And the present invention becomes more safe and effective, and the knife is convenient for promotion and application too;

4. The present invention can also be used in other advanced techniques such as natural orifice transluminal endoscopic surgeries (NOTES). And the present invention has an extensive application prospect and may bring huge economic and social benefits.

By means of the knife, a multi-angle movement of a cutting knife blade of the endoscopy knife can be achieved, wherein the movement includes a circumstance cutting by the knife blade in parallel with mucosal tissues. And the knife blade angle is not limited by the lens of the endoscope, so that the speed and the quality of the endoscopy therapy are greatly improved, and subsidiary injuries potentially occurring to peripheral tissues are minimized to the furthest.

Figure 1:
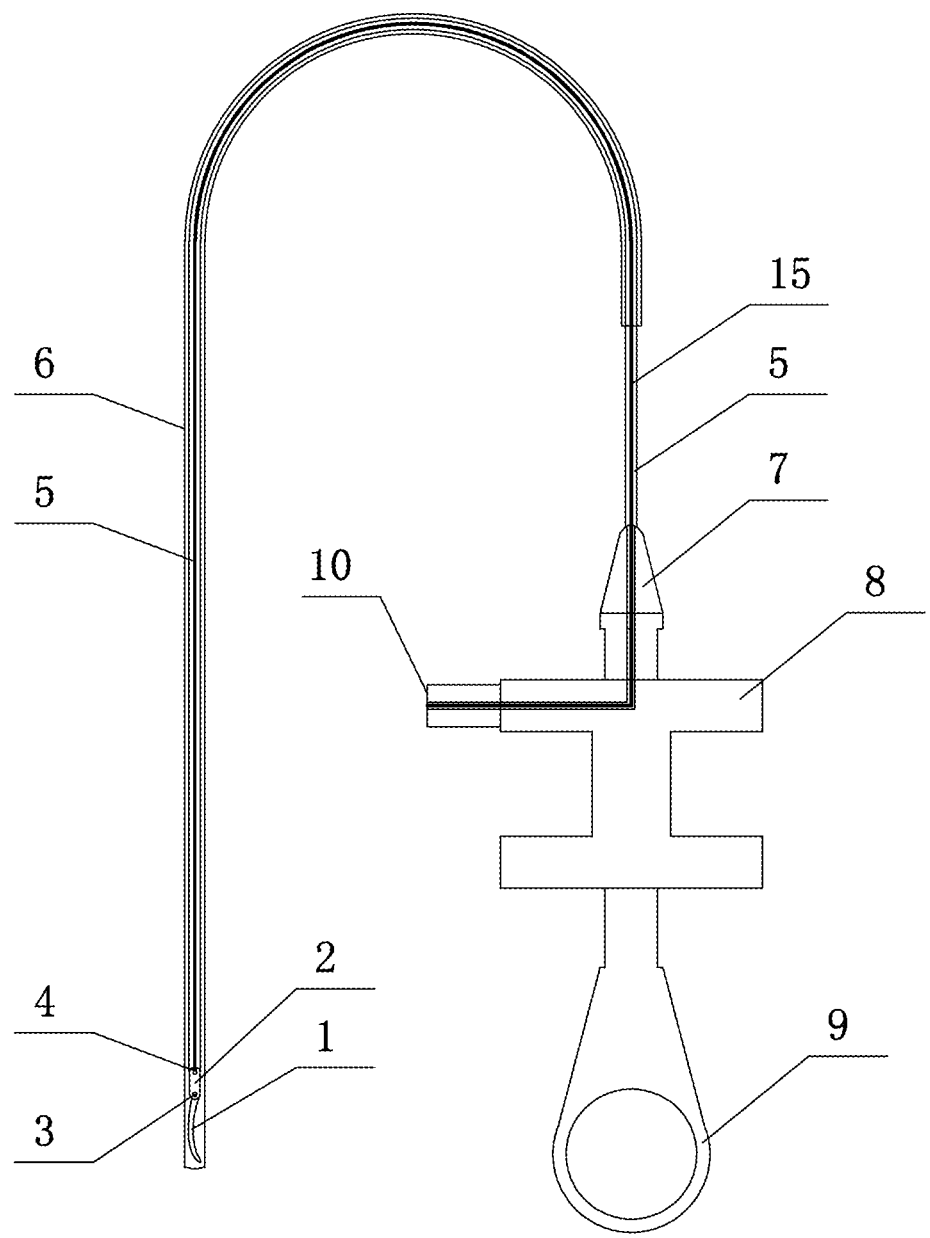
FIG. 1 is a structure diagram of the present invention.

Reference signs of drawings: 1—knife head, 2—knife base, 3—transverse joint, 4—longitudinal joint, 5—knife body, 6—outer sheath, 7—handle, 8—sliding rod, 9—pull ring, 10—power port, 11—knife edge, 12—knife back, 13—clamping pieces, 14—knife groove, 15—guide wire, 16—knife head root, 17—knife head shaft, 18—compression spring, 19—shaft base, 20—knife base shaft, 21—torsion spring, 22—base shaft groove, 23—guide-wire channel, 24—guide-wire cavity, 25—sliding rod core, 26—guide-wire outlet, 27—sliding groove.

DETAILED DESCRIPTION OF THE EMBODIMENTS

The double-joint sickle knife for an endoscopy therapy is described in detail with reference to the accompanying drawings and the embodiments as follows.

As shown in FIG. 1 to FIG. 4, a double-joint sickle knife for an endoscopy therapy of one embodiment. The knife comprises a knife head 1, a knife base 2, a knife body 5, a guide wire 15, a handle 7 and a sliding rod 8. The knife head 1 is connected with one end of the knife base 2 by a transverse joint 3. And the other end of the knife base 2 is connected with a head end of the knife body 5 by a longitudinal joint 4. The tail end of the knife body 5 is connected with one end of the handle 7, and the sliding rod 8 for adjusting the transverse joint 3 is arranged on the handle 7. One end of the guide wire 15 is connected with the knife head 1, and the guide wire 15 passes through the knife base 2, the knife body 5, the handle 7 and the sliding rod 8 successively. And the other end of the guide wire 15 is connected with a power port 10. The transverse joint 3 can be rotated by controlling the sliding rod 8, so that the knife head 1 moves transversely to achieve a cutting operation. The knife head 1 comprises a knife edge 11, a knife back 12 and a knife head root 16. The knife back 12 is made of an insulating ceramic material. The knife edge 11 is made up by embedding the electric conductive guide wire 15 into the knife back 12. Moreover, the head end of the guide wire 15 forms the knife edge 11. One end of the knife base 2 connected with the knife head 1 is divided into two up and down clamping pieces 13 which are parallel to each other. And the space between the two clamping pieces 13 forms a knife groove 14. One end of the knife 1 connected with the knife base 2 is a knife head root 16. And the knife head root 16 is putted into the knife groove 14. And the knife head root 16 is equipped with a knife head shaft 17. And the knife head shaft 17 is embedded with the two clamping pieces 13. A side of the knife head root 16 near the knife back 12 is connected with the knife base 2 by the compression spring 18. And all the above-mentioned structures form the transverse joint 3. All the above-mentioned structures form the transverse joint 3. A rotated transverse joint can be pulled back to a functional position by the compression spring 18 in the transverse joint 3.

One end of the knife body 5 connected with the knife base 2 is equipped with two shaft bases 19. A concave base shaft groove 22 is arranged in the middle of the tail end of the knife base 2. The knife base shaft 20 crosses the one end of the knife body 5 connected with the knife base 2 and protrudes outwardly. And both ends of the knife base shaft 20 are inserted into the two shaft bases 19 respectively. A torsion spring 21 wraps around the knife base shaft 20 and is put into the base shaft groove 2. Two forwardly and backwardly protruding branches of the torsion spring 21 are inserted into the knife base 2 and the knife body 5 respectively. All the above mentioned structures form the longitudinal joint 4. The torsion spring 21 in the longitudinal joint 4 has features such as resilience and damping. A guide-wire cavity 24 is arranged in the knife body 5, and the guide wire 15 is arranged in the guide-wire cavity 24. A guide-wire channel 23 is arranged on the knife base 2 and a head end of the knife body 5, and the guide-wire channel 23 is connected with the guide-wire cavity 24. An outer sheath 6 is sleeved on the outside of the knife body 5, and the outer sheath 6 can move on the knife body 5 and wrap the knife head 1, so as to choose whether to expose the knife head 1 according to the requirement to avoid injuring an endoscope tube or a mucosa in the therapy view field. The sliding rod 8 is H-shaped. And the middle part of the sliding rod 8 is annular and cylindrical, and covers around the outside of the handle 7. A hollow sliding groove 27 is arranged in the handle 7. And a rectangular column sliding rod core 25 is arranged in the middle of the sliding rod 8. And the sliding rod core 25 crosses into the sliding groove 27. And a guide-wire outlet 26 is arranged at the top of the sliding rod core 25. And the guide wire 15 passes through the upper end of the sliding rod 8 by the guide-wire outlet 26 and is connected with the power port 10. And the other end of the handle 7 is connected with a round pull ring 9.

Figure 2:
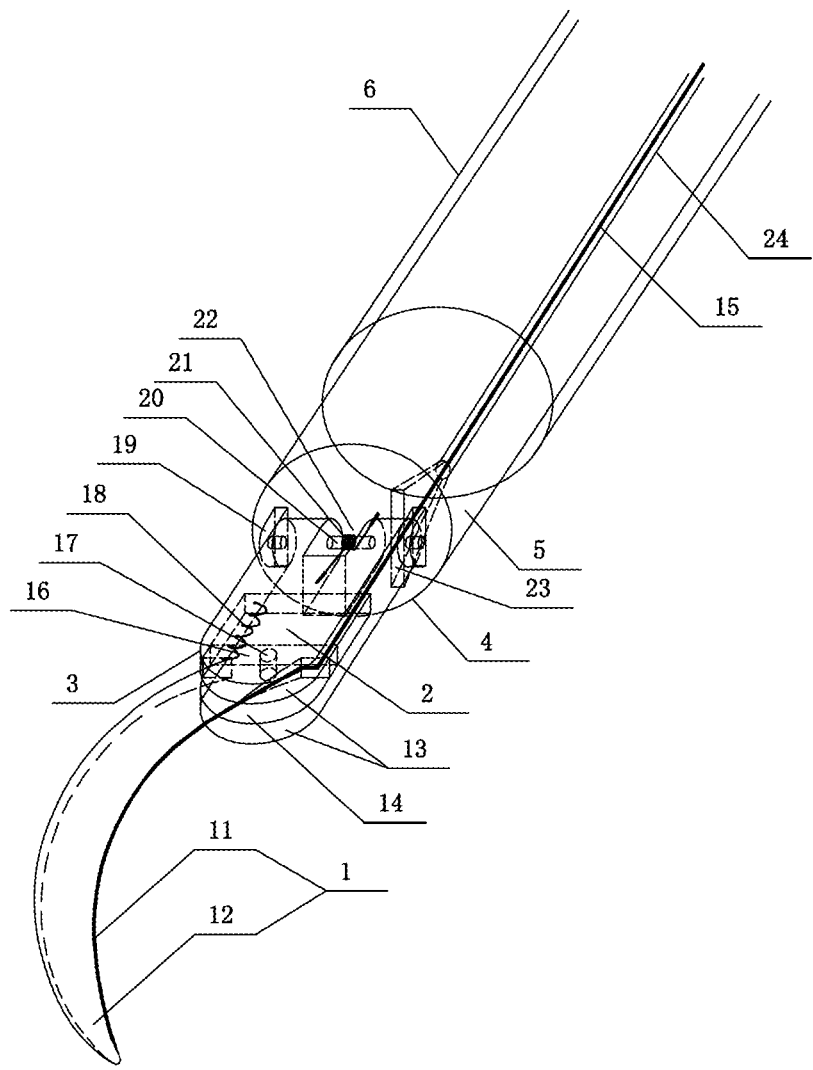
FIG. 2 illustrates in detail a knife head, a knife base, a knife body, a transverse joint and a longitudinal joint of the present invention.

FIG. 2 illustrates in detail the knife head 1, the knife base 2, a knife body 5, the transverse joint 3 and the longitudinal joint 4 of the present invention. The knife head 1 comprises a knife edge 11, a knife back 12 and a knife head root 16. The knife back 12 is made of an insulating ceramic material. And the knife edge 11 is embedded into the knife back 12 in the horizontal half plane of the cross section by the electronic guide wire 15. The head end of knife base 2 is divided into two up and down clamping pieces 13 which are parallel to each other, the space between the two clamping pieces 13 forms a knife groove 14. The tail end of knife head 1 is a T-shaped knife head root 16. And the knife head root 16 is putted into the knife groove 14. The knife head shaft 17 lies at the middle of the knife head root 16, and is embedded into the two up and down clamping pieces 13. And a side of the knife head root 16 near the knife back 12 is connected with the knife base 2 by the compression spring 18. The above-mentioned structures form the transverse joint 3. The cylindrical knife base shaft 20 crosses the tail end of the knife base 2, and its two ends protrude outwardly. And the cylindrical knife base shaft 20 is inserted into the two shaft bases 19 protruding outwardly from a head end of the knife body 5. A concave base shaft groove 22 is arranged in the middle of the tail end of the knife base 2. In the concave base shaft groove 22, the torsion spring 21 wraps around the knife base shaft 20; and two forwardly and backwardly protruding branches of the torsion spring 21 are inserted into the knife base 2 and the knife body 5 respectively. And the above mentioned structures form the longitudinal joint 4. A longitudinal strip guide-wire channel 23 is arranged in the cross section of the head end of the knife body 5. And the guide-wire channel 23 extends to the tail end narrowly from the internal of the knife body 5, and is connected with the guide-wire cavity 24.

Figure 3:
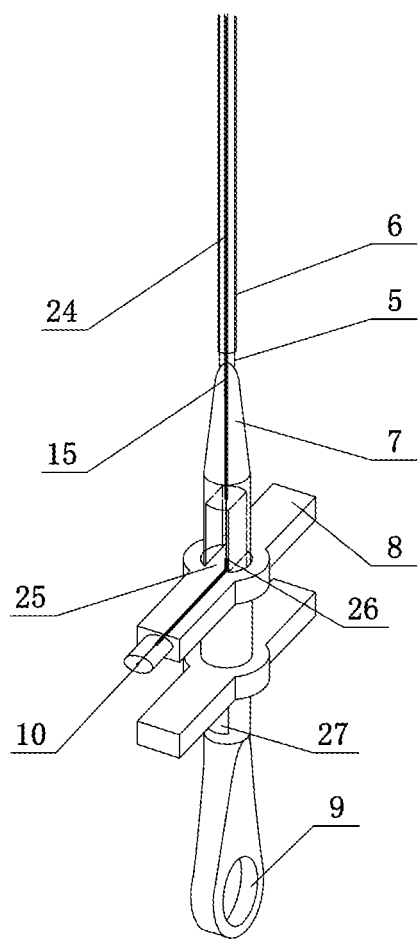
FIG. 3 illustrates in detail a handle and a sliding rod of the present invention.

FIG. 3 illustrates in detail a part of a handle 7 and a sliding rod 8 of the present invention, The tail end of the knife body 5 is connected with the head end of the handle 7, and the head end of handle 7 is a little thicker than the outer sheath 6, in order to avoid the outer sheath 6 from sliding and slipping. And a hollow sliding groove 27 is arranged in the handle 7. And the sliding rod 8 is H-shaped. The middle part of the sliding rod 8 is annular and cylindrical, and covers around the outside of the handle 7. And the rectangular column sliding rod core 25 is arranged in the middle of the sliding rod 8. The sliding rod core 25 crosses into the groove 27. And a guide-wire outlet 26 is arranged at the top of the sliding rod core 25. And a round pull ring 9 is arranged at the tail end of the handle 7. The guide-wire cavity 24 passes through from the internal of the knife body 5 to the head end of the handle 7, and ends at the top of the sliding rod groove 27 in the handle 7. Please refer to FIG. 2 and FIG. 3, the guide wire 15 passes through the knife head root 16, the knife base 2, the guide-wire channel 23, the guide-wire cavity 24, the handle 7, and the sliding rod core 25 successively from the knife edge 11 to the tail part, until the guide wire 15 is connected with the power port 10.

Figure 4:
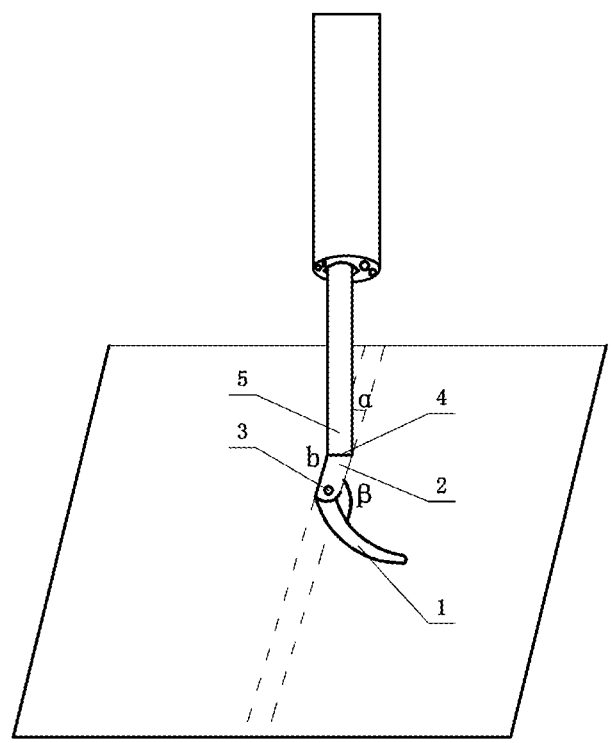
FIG. 4 illustrates the plane d relative to the knife protruding outwardly from the endoscope biopsy channel of the present invention.

FIG. 4 illustrates a plane d relative to the knife protruding outwardly from the endoscope biopsy channel of the present invention. The knife body 5 forms an α (alpha) Angle relative to a plane a. The plane where the α Angle is in perpendicular to the plane d. And the knife head 1 forms a β (Beta) angle relative to the knife base 2, and a proper angle is arranged between the plane d and the plane where the β Angle is, or the plane d is in parallel with the plane where the β Angle is.

In a digestive endoscopy minimally invasive surgery, the knife head 1 and knife base 2 of the present double-joint sickle knife can be sent to the surgical site through the endoscope biopsy channel. The power port 10 on the sliding rod 8 of the external handle is connected with a high frequency power generator. The knife edge 11 generates a cutting action by being powered on through the conductive guide wire. The knife head 1 is sickle-shaped, and only has a cutting function on the knife edge 11 in the working surface. The knife back 12 is made of a ceramic material, so as to prevent subsidiary injuries effectively. The knife base 2 is pressed down to force the longitudinal joint 4 to rotate so as to adjust the α Angle by operating the endoscope (as shown FIG. 4), so that the knife head 1 can be placed at different angles relative to the plane of the therapy view field, and even in parallel with the plane of the therapy view field. The torsion spring 21 in the internal of the longitudinal joint 4 provides the joint with functions of resilience and damping in a proper intensity.

The guide wire 15 can be pulled back by the sliding rod 8 so as to force knife head 1 to carry a rotating movement around the knife head shaft 17, so that the transverse joint 3 can rotate to adjust the angle β (as show in FIG. 4). The axial movement of knife head 1 can be controlled just by the index finger and the middle finger to pull back the sliding rod 8 so as to achieve a intricate cutting action. A rotated transverse joint can be pulled back to the functional position by the compressed spring 18 in the transverse joint 3 (the state as shown in FIG. 1 and FIG. 2). When the fingers loose the sliding rod 8, by adjusting the two joints in different directions and quadrants, the cutting angle of the knife edge 11 can be wider in the range, the endoscopic view can be clearer, and it can be easily and quickly to cut and peel lesions.

The description above are merely illustrative, is not intended to limit the invention. The description of the present invention is readily appreciated by those skilled in the art can that, any modification, improvement, or equivalent replacement of the present invention within the spirit and principle of the present invention should be deemed to fall within the protection scope of the present invention.

What is claimed is:

1. A double-joint sickle knife for an endoscopy therapy comprising a sickle-shaped knife head, a knife base, a knife body, a guide wire, a handle and a sliding rod; wherein the knife head is connected with one end of the knife base by a first, transverse joint that is parallel with a plane of therapy view field, and the other end of the knife base is connected with a head end of the knife body by a second, longitudinal joint that is perpendicular to the plane of therapy view field; a tail end of the knife body is connected with one end of the handle, and the sliding rod is arranged on the handle; one end of the guide wire is connected with the knife head, and the guide wire passes through the knife base, the knife body, the handle and the sliding rod successively; and the other end of the guide wire is connected with a power port; wherein pulling back the guide wire via the sliding rod causes the first joint to rotate and pressing down the guide wire causes the second joint to rotate wherein, the knife head comprises a knife edge, a knife back and a knife head root, said knife head root formed on the end of the knife head which connected with the knife base, wherein: the end of the guide wire connected with the knife head forms the knife edge; the one end of the knife base connected with the knife head is divided into two up and down clamping pieces which are parallel to each other: and a space between the two clamping pieces forms a knife groove; and the knife head root is positioned in the knife groove; and the knife head root is equipped with a knife head shaft; and the knife head shaft is embedded with the two clamping pieces; a side of the knife head root near the knife back is connected with the knife base by a compression spring; and the knife base, the two clamping pieces, and the knife head root form the first, transverse joint.

2. The double-joint sickle knife for an endoscopy therapy as claimed in claim 1, wherein, the knife back is made of an insulating ceramic material; and the knife edge is made from a metallic material.

3. The double-joint sickle knife for an endoscopy therapy as claimed in claim 1, wherein: the head end of the knife body connected with the knife base is equipped with two shaft bases; a concave base shaft groove is arranged in a middle of a tail end of the knife base; a knife base shaft crosses the head end of the knife body connected with the knife base and protrudes outwardly; and both ends of the knife base shaft are inserted into the two shaft bases respectively; a torsion spring wraps around the knife base shaft and is positioned in the base shaft groove; two forwardly and backwardly protruding branches of the torsion spring are inserted into the knife base and the knife body respectively; the head end of the knife body, the knife base, the two shaft bases, and the knife base shaft form the second, longitudinal joint.

4. The double-joint sickle knife for an endoscopy therapy as claimed in claim 1, wherein: a guide-wire cavity is arranged in the knife body, and the guide wire is set in the guide-wire cavity.

5. The double-joint sickle knife for an endoscopy therapy as claimed in claim 4, wherein, a guide-wire channel is arranged on the knife base and the knife body, and the guide-wire channel is connected with the guide-wire cavity.

6. The double-joint sickle knife for an endoscopy therapy as claimed in claim 1, wherein, an outer sheath is sleeved on an outside of the knife body, and the outer sheath is movable on the knife body and wraps the knife head.

7. The double-joint sickle knife for an endoscopy therapy as claimed in claim 1, wherein, the sliding rod is H-shaped; and a middle part of the sliding rod is annular and cylindrical, and covers around an outside of the handle; a hollow sliding groove is arranged in the handle; and a rectangular column sliding rod core is arranged in a center of the sliding rod; and the sliding rod core crosses into the sliding groove; and a guide-wire outlet is arranged at a top of the sliding rod core; and the guide wire passes through an upper end of the sliding rod by the guide-wire outlet and is connected with the power port.

8. The double-joint sickle knife for an endoscopy therapy as claimed in claim 1, wherein, the other end of the handle is connected with a round pull ring.

* * * * *